United States Patent
Ohba et al.

(10) Patent No.: US 10,493,091 B2
(45) Date of Patent: Dec. 3, 2019

(54) METHOD FOR STORING $P^1$, $P^4$-BIS(5'-URIDYL)TERAPHOSPHATE CRYSTALS

(71) Applicant: Yamasa Corporation, Choshi-shi, Chiba (JP)

(72) Inventors: Yusuke Ohba, Choshi (JP); Kentaro Miyoshi, Choshi (JP); Fumitaka Kano, Choshi (JP)

(73) Assignee: Yamasa Corporation, Choshi-shi (JP)

( * ) Notice: Subject to any disclaimer, the term of this patent is extended or adjusted under 35 U.S.C. 154(b) by 47 days.

(21) Appl. No.: 15/738,108

(22) PCT Filed: Jun. 28, 2016

(86) PCT No.: PCT/JP2016/069182
§ 371 (c)(1),
(2) Date: Dec. 19, 2017

(87) PCT Pub. No.: WO2017/002827
PCT Pub. Date: Jan. 5, 2017

(65) Prior Publication Data
US 2018/0161355 A1  Jun. 14, 2018

(30) Foreign Application Priority Data

Jun. 29, 2015 (JP) ................................ 2015-129944

(51) Int. Cl.
| | |
|---|---|
| *A61K 31/7084* | (2006.01) |
| *A61J 3/00* | (2006.01) |
| *C07H 21/02* | (2006.01) |
| *C30B 29/60* | (2006.01) |
| *C07H 1/06* | (2006.01) |

(52) U.S. Cl.
CPC ............. *A61K 31/7084* (2013.01); *A61J 3/00* (2013.01); *C07H 1/06* (2013.01); *C07H 21/02* (2013.01); *C30B 29/605* (2013.01)

(58) Field of Classification Search
None
See application file for complete search history.

(56) References Cited

U.S. PATENT DOCUMENTS

| | | | |
|---|---|---|---|
| 6,458,946 B1 * | 10/2002 | Maeda | C07H 19/10 536/26.21 |
| 2004/0014713 A1 | 1/2004 | Yerxa et al. | |

FOREIGN PATENT DOCUMENTS

| | | |
|---|---|---|
| EP | 1043329 A1 | 10/2000 |
| EP | 1191032 A1 | 3/2002 |
| EP | 2045257 A1 | 4/2009 |
| EP | 2832359 A1 | 2/2015 |
| WO | WO2000/020430 A1 | 4/2000 |
| WO | WO2013/146649 A1 | 10/2013 |

OTHER PUBLICATIONS

WIPO, Japanese International Search Authority, International Search Report and Written Opinion dated Sep. 13, 2016 in International Patent Application No. PCT/JP2016/069182, 8 pages.
European Patent Office, Extended European Search Report dated Jan. 11, 2019 in European Patent Application No. 16817935, 11 pages.
"Summary and examination overview of documents submitted pertaining to the drug master file of Diquas ophthalmic solution 3%" in Office Action dated Jul. 17, 2018 in JP Patent Application No. 2017-526381.
"Diquas ophthalmic Solution 3% / Pharmaceutical Interview Form" in Office Action dated Jul. 17, 2018 in JP Patent Application No. 2017-526381.
Office Action dated Jul. 17, 2018 in JP Patent Application No. 2017-526381.

\* cited by examiner

*Primary Examiner* — Dale R Miller
(74) *Attorney, Agent, or Firm* — Masuvalley & Partners

(57) ABSTRACT

[Problem] Provided is a method for easily and stably storing crystals of $P^1,P^4$-bis(5'-uridyl)tetraphosphate for a long term.
[Solution] A method for storing packed crystals of $P^1,P^4$-bis(5'-uridyl)tetraphosphate or a pharmaceutically acceptable salt thereof, wherein one of the following storage conditions (1) to (3): (1) a storage temperature of 0° C. or more and less than 25° C.; (2) a storage temperature of 25° C. or more and less than 40° C. and a crystal pH of 4.5 to 8.0; and (3) a storage temperature of 40° C. or more and less than 60° C. and a crystal pH of 5.0 to 6.4 is selected and the crystals of $P^1,P^4$-bis(5'-uridyl)tetraphosphate or the pharmaceutically acceptable salt thereof are stored under the selected condition.

2 Claims, 1 Drawing Sheet

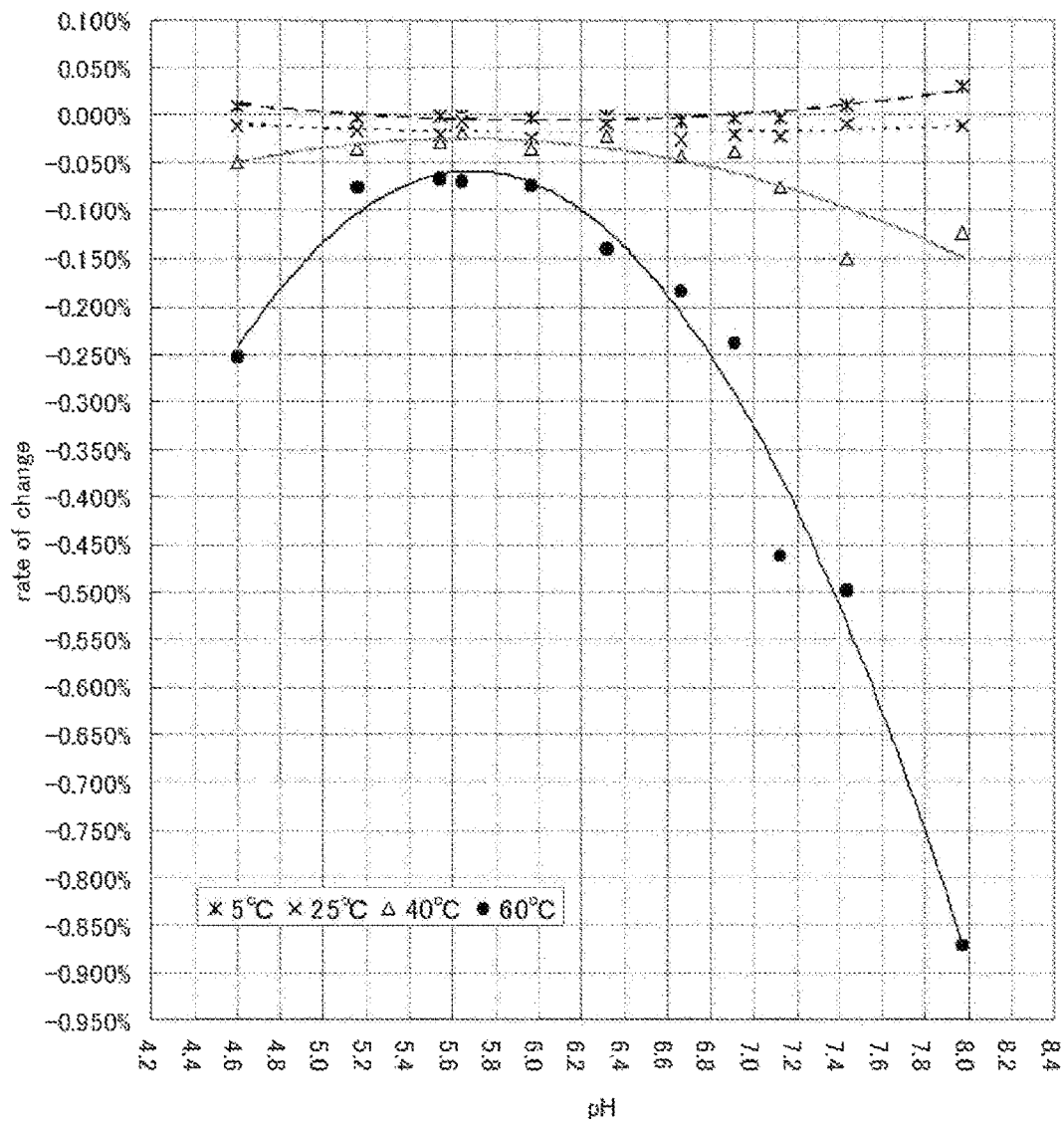

METHOD FOR STORING P¹, P⁴-BIS(5'-URIDYL)TERAPHOSPHATE CRYSTALS

RELATED APPLICATIONS

This application is the U.S. National Phase of and claims priority to International Patent Application No. PCT/JP2016/069182, International Filing Date Jun. 28, 2016, entitled Method For Storing $P^1$, $P^4$-bis(5'-Uridyl)Tetraphosphate Crystals; which claims benefit of Japanese Patent Application No. JP2015-129944 filed Jun. 29, 2015; both of which are incorporated herein by reference in their entireties.

TECHNICAL FIELD

The present invention relates to a method for stably storing $P^1,P^4$-bis(5'-uridyl)tetraphosphate crystals.

BACKGROUND ART $P^1,P^4$-bis(uridyl)tetraphosphate (trivial name: "$UP_4U$") represented by the formula [I] below or its salts are used as therapeutic agents for keratoconjunctival epithelial disorders due to dry eye. Furthermore, the above compounds have the effect of inducing expectoration and are therefore expected to be developed as expectorants or therapeutic agents for pneumonia.

[Chem. 1]

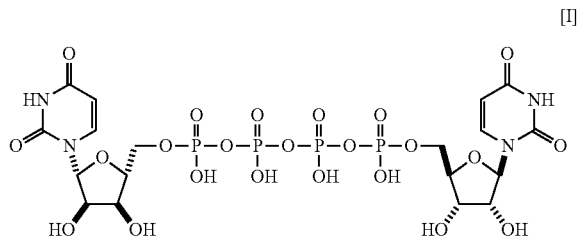

[I]

In order to enable $P^1,P^4$-bis(5'-uridyl)tetraphosphate (hereinafter also referred to as "$UP_4U$") to be stably stored, crystals of this compound or a salt thereof are obtained (see Patent Literature 1). However, the conventional literature states that the crystals are stable as compared with a lyophilized product, but does not consider under what condition the crystals can be stably stored.

CITATION LIST

Patent Literature

Patent Literature 1: WO2000/020430

SUMMARY OF INVENTION

Technical Problem $UP_4U$ is a compound for use as a raw material for pharmaceutical products. In the case of using $UP_4U$ as a raw material for pharmaceutical products, its intermediate product having an extremely high purity needs to be used in order to minimize the production of by-products derived from impurity contained therein. In some cases, such a severe standard that 0.1% impurities become a problem may be required. Therefore, in storing the produced intermediate product, it is necessary to set a condition under which its decomposition can be suppressed as much as possible. However, it has not at all heretofore been known what condition contributes to the decomposition and what condition setting can suppress the decomposition.

Solution to Problem

Hence, a challenge of the present invention is to provide a method for easily and stably storing $UP_4U$ crystals for a long term.

The inventors have conducted intensive studies to solve the above problem and resulted in the finding that the stability of $UP_4U$ crystals significantly varies depending on the storage temperature and pH of the crystals. The inventors have conducted further studies, resulted in the finding that when the $UP_4U$ crystals are stored under one of the following conditions (1) to (3): (1) a storage temperature of 0° C. or more and less than 25° C.; (2) a storage temperature of 25° C. or more and less than 40° C. and a crystal pH of 4.5 to 8.0; and (3) a storage temperature of 40° C. or more and less than 60° C. and a crystal pH of 5.0 to 6.4, the rate of change in HPLC purity of the crystals at four weeks of storage can be held to 0.15% or less and, therefore, the rate of decrease in HPLC purity of the crystals during storage can be reduced, and finally completed the present invention based on these findings.

Advantageous Effects of Invention

With the use of the storage method according to the present invention, $UP_4U$ can be stored in a stable state for a long term without substantially decomposing it.

BRIEF DESCRIPTION OF DRAWINGS

FIG. 1 shows the rates of change (%) in HPLC purity of different types of $UP_4U$ crystals exhibiting different crystal pHs when each type of $UP_4U$ crystals were packed in a container and stored at some temperatures from 5° C. to 60° C. for four weeks. The graph shows as legends * representing 5° C., x representing 25° C., Δ representing 40° C., and ● representing 60° C., and also shows respective fitted curves at these temperatures.

DESCRIPTION OF EMBODIMENTS

The storage method according to the present invention relates to a method for storing $UP_4U$ crystals. $UP_4U$ for use as crystals may be in the form of a free base or a pharmaceutically acceptable salt. Specific examples of the salt are pharmaceutically acceptable salts, including alkali metal salts, such as sodium salts and potassium salts, alkaline earth metal salts, such as calcium salts and magnesium salts, and ammonium salts. Examples of the salt in terms of number of hydrogens substituted include those obtained by substitution with one to four metal atoms.

In the storage method according to the present invention, in order to hold the rate of change in HPLC purity of $UP_4U$ crystals at four weeks of storage to 0.15% or less, the $UP_4U$ crystals are stored under one of the following conditions (1) to (3): (1) a storage temperature of 0° C. or more and less than 25° C.; (2) a storage temperature of 25° C. or more and less than 40° C. and a crystal pH of 4.5 to 8.0; and (3) a storage temperature of 40° C. or more and less than 60° C. and a crystal pH of 5.0 to 6.4.

Furthermore, in the storage method according to the present invention, in order to hold the rate of change in the HPLC purity of the $UP_4U$ crystals at four weeks of storage to 0.10% or less, the $UP_4U$ crystals are stored under one of the following conditions (4) to (6): (4) a storage temperature of 0° C. or more and less than 25° C.; (5) a storage temperature of 25° C. or more and less than 40° C. and a crystal pH of 4.5 to 7.4; and (6) a storage temperature of 40° C. or more and less than 60° C. and a crystal pH of 5.2 to 6.2.

Moreover, in the storage method according to the present invention, in order to hold the rate of change in the HPLC purity of the $UP_4U$ crystals at four weeks of storage to 0.05% or less, the $UP_4U$ crystals are stored under one of the following conditions (7) and (8): (7) a storage temperature of 0° C. or more and less than 25° C.; and (8) a storage temperature of 25° C. or more and less than 40° C. and a crystal pH of 4.6 to 6.6.

The term crystal pH in the present invention refers to the value of pH of crystals measured with 1 g of crystals dissolved in 20 mL of water. The control of the pH of $UP_4U$ crystals within a desired range of values is possible, for example, by controlling the pH of an original solution for use in crystallization. To control the pH, it is sufficient to use, as necessary, an arbitrary acid or alkali capable of being used for production of raw materials or the like for pharmaceutical products. An arbitrary one selected from hydrochloric acid, nitric acid, phosphoric acid, and so on can be used as the acid and an arbitrary one selected from sodium hydroxide, sodium carbonate, sodium hydrogen carbonate, and so on can be used as the alkali.

$UP_4U$ for use in the present invention can be synthesized and crystallized by any known method (for example, Patent Literature 1). In a specific example, $UP_4U$ crystals can be obtained by synthesizing crude $UP_4U$ by an arbitrary production method, such as chemical synthesis or enzymatic synthesis, refining the crude $UP_4U$ using anion-exchange chromatography and activated carbon chromatography, and adding a hydrophilic organic solvent into a solution of the refined $UP_4U$. However, the crystals may be those obtained by other methods so long as the crystals can be obtained. Furthermore, the obtained crystals can be appropriately dried by an ordinary method, such as reduced-pressure drying, through-circulation drying or drying by heating.

Considering that the obtained $UP_4U$ crystals are for use in pharmaceutical products, they have preferably a purity of 95% or more, more preferably 97% or more, and still more preferably 99% or more. Furthermore, these crystals may carry adhering water or may be a hydrate. More specifically, three to eight molecules of water may bind or adhere to one molecule of $UP_4U$.

In the method according to the present invention, the $UP_4U$ crystals are stored in a state packed in an arbitrary container. The container that can be used for storage is a container having an arbitrary shape, such as a pouch, a bottle, a can, a box, an ampule.

Materials for the container that can be used include unstretched, uniaxially or biaxially stretched films made of polyolefin resins, such as low-density polyethylenes and high-density polyethylenes, vinyl resins, such as polystyrene and polyvinyl chloride, polyamide resins, such as nylon 6 and nylon 66, polyester resins, such as polyethylene terephthalate and polytetramethylene terephthalate.

These film materials can be used in a single layer or a laminate formed of two or more layers or can be used in a laminate of metal foils, such as aluminum, or a laminate of deposited metal or metal oxide films. Furthermore, the container may be stored in a two-ply, three-ply or more multi-ply form. The packing state of the container is preferably a non-open state, such as closed, airtight or sealed state, and more preferably a sealed or airtight state.

If $UP_4U$ is stored under conditions where the crystal pH or the temperature is out of the above ranges, $UP_4U$ becomes likely to decompose, which causes the risk that $UP_4U$ becomes unsuitable when used as raw materials or the like for pharmaceutical products.

The method according to the present invention can hold the decrease in high-performance liquid chromatography (HPLC) purity of $UP_4U$ at four weeks of storage to 0.15% or less, 0.10% or less, or even 0.05% or less, which is extremely suitable for suppressing decomposition.

Specifically, for example, when in storing $UP_4U$ the decrease in HPLC purity of $UP_4U$ as active ingredients for production of pharmaceutical products is required to be less than 0.15%, $UP_4U$ is stored in a closed, sealed or airtight state under one of the following storage conditions: (1) a storage temperature of 0° C. or more and less than 25° C.; (2) a storage temperature of 25° C. or more and less than 40° C. and a crystal pH of 4.5 to 8.0; and (3) a storage temperature of 40° C. or more and less than 60° C. and a crystal pH of 5.0 to 6.4. So long as $UP_4U$ is in a storage environment where the storage temperature can be controlled at 0° C. or more and less than 25° C., there is no need to control the crystal pH. However, when the temperature of the storage environment is not stable and may reach 25° C. or more and less than 40° C., the crystal pH needs to be controlled at 4.5 to 7.4 in order to hold the decrease in HPLC purity of $UP_4U$ at four weeks of storage to less than 0.15%. When the above temperature may further increase to 40° C. or more and less than 60° C., the crystal pH is controlled at 5.2 to 6.2.

Likewise, in order to hold the decrease in HPLC purity of $UP_4U$ to less than 0.10%, $UP_4U$ needs to be stored under one of the following storage conditions: (4) a storage temperature of 0° C. or more and less than 25° C.; (5) a storage temperature of 25° C. or more and less than 40° C. and a crystal pH of 4.5 to 7.4; and (6) a storage temperature of 40° C. or more and less than 60° C. and a crystal pH of 5.2 to 6.2.

Furthermore, in order to hold the decrease in HPLC purity of $UP_4U$ to less than 0.05%, $UP_4U$ is stored under one of the following storage conditions: (7) a storage temperature of 0° C. or more and less than 25° C.; and (8) a storage temperature of 25° C. or more and less than 40° C. and a crystal pH of 4.6 to 6.6.

Taken together, (A) when the storage temperature is kept at 0° C. or more and less than 25° C., substantially no decrease in HPLC purity of $UP_4U$ crystals occur regardless of the crystal pH of $UP_4U$ and, therefore, this condition is suitable for long-term storage of the $UP_4U$ crystals. On the other hand, in order to store $UP_4U$ crystals under an environment where the temperature control is difficult, it is necessary to control the crystal pH within a specified range by controlling the pH of the original solution of the crystals.

(B) When the storage temperature may reach 25° C. or more and less than 40° C., the crystal pH is set at 4.5 to 8.0, preferably 4.5 to 7.4, and more preferably 4.6 to 6.6. This is preferred because the decrease in HPLC purity of the crystals at four weeks of storage can be thus held to 0.15% or less, 0.10% or less, and 0.05% or less, respectively.

(C) When the storage temperature may reach 40° C. or more and less than 60° C., the decrease in HPLC purity of the crystals at four weeks of storage can be held to 0.15% or less and 0.10% or less by setting the crystal pH at 5.0 to 6.4 and preferably 5.2 to 6.2, respectively. When it is necessary to hold the decrease in HPLC purity to 0.05% or less, a storage temperature exceeding 40° C. is not preferred.

(D) Furthermore, reaching a storage temperature of 60° C. or more is not preferred because the HPLC purity of the crystals may significantly decrease regardless of the crystal pH.

Moreover, in order to hold the decrease in HPLC purity of $UP_4U$ crystals to a desired value or less when they are stored for more than four weeks (two or three months), it is necessary to set the storage temperature at 0° C. or more and less than 25° C. or set the crystal pH within more preferable ranges of crystal pHs than within the ranges thereof described to be necessary for the respective temperature regions in the above (B) and (C).

EXAMPLES

Hereinafter, the present invention will be described in specific terms with reference to examples but is not at all limited to these examples.

Example 1

Control of $UP_4U$ Crystals with Different pHs $UP_4U$ crystals prepared by a known method were dissolved in deionized water. Various phosphoric acid aqueous solutions or sodium hydroxide aqueous solutions were each added to the solution containing $UP_4U$ dissolved therein to prepare solutions having different pHs (hereinafter, referred to as "original solutions").

Ethanol was put into each of the original solutions to make the original solution lightly cloudy, followed by addition of a small amount of $UP_4U$ crystals and stirring for a dozen hours. After confirmation of crystal precipitation, ethanol was further put into each of the solutions, the solution was stirred, and crystals were then separated from the solution using a centrifuge. The obtained various crystals were dried with a circulation dryer to prepare various $UP_4U$ crystals having different pHs.

(pH Measurement) Water was sufficiently boiled and then cooled in a state where a carbon dioxide absorption tube was connected, thus preparing distilled water. An amount of 1.0 g of each test sample was dissolved in 20 mL of the prepared distilled water. The pH (crystal pH) of this solution was measured. Table 1 below shows the correspondences between the pHs of the original solutions prepared before being crystallized and the crystal pHs.

Example 2

Stability Test (Packing of Test Sample) An amount of approximately 20 mg of each test sample was put into a pouch made of low-density polyethylene and sealed by heat sealing. This pouch was further put into a pouch made of low-density polyethylene and sealed by heat sealing. This pouch was still further put into a pouch made of low-density polyethylene and sealed by heat sealing. This pouch was put into a pouch made of aluminum-metallized film and sealed by heat sealing, thus preparing a sample for stability test.

(Stability Test) Packed samples were put into thermostatic baths at 5° C., 25° C., 40° C., and 60° C., respectively, and stored for four weeks.

(Analysis) For each sample zero days after the start of the stability test and samples of the same type at four weeks of storage at the different temperatures, the packing by sealing was opened and each of the test samples was dissolved in deionized water. This solution was analyzed by HPLC and, based on the analysis result, evaluated in terms of stability. The conditions of the measurement using HPLC in this analysis were as follows.

TABLE 2

| | |
|---|---|
| System | Waters 2695,2487 |
| Column | Zorbax Eclipse XDB-C18, S-5 um, 250 × 4.6 mmI.D. |
| Guard Column | Zorbax Eclipse XDB-C18 12.5 × 4.6 mm |
| Temperature | 30° C. |
| Measurement Wavelength | 262 nM |
| Flow | 1.0 mL/min. |
| Mobile Phase | MeOH/Buffer = 16/84 |
| Buffer | 10 mM TBA-HSO4 (3.4 g/L) |
| | 80 mM KH2PO4 (10.89 g/L) |
| | pH 6.7 ± 0.1 by KOH (2.2 g/L) |

The evaluation was made by defining the value obtained by subtracting the HPLC purity (%) of crystals zero days after the start of the stability test from the HPLC purity (%) of the crystals at four weeks of storage as a rate of change (%). The rate of changes (%) under the different conditions are shown in Table 3 and FIG. 1.

TABLE 1

| | | | | | | | | | | | |
|---|---|---|---|---|---|---|---|---|---|---|---|
| Orginal Liquid pH | 2.50 | 3.00 | 3.50 | 4.00 | 5.50 | 6.50 | 7.40 | 7.80 | 8.00 | 8.10 | 8.20 |
| Crystal pH | 4.60 | 5.16 | 5.54 | 5.64 | 5.97 | 6.32 | 6.66 | 6.91 | 7.12 | 7.43 | 7.97 |

TABLE 3

| pH | 4.60 | 5.16 | 5.54 | 5.64 | 5.97 | 6.32 | 6.66 | 6.91 | 7.12 | 7.43 | 7.97 |
|---|---|---|---|---|---|---|---|---|---|---|---|
| 5° C. | 0.01 | 0.00 | 0.00 | 0.00 | 0.00 | 0.00 | −0.01 | 0.00 | 0.00 | 0.01 | 0.03 |
| 25° C. | −0.01 | −0.02 | −0.02 | −0.01 | −0.02 | −0.01 | −0.03 | −0.02 | −0.02 | −0.01 | −0.01 |
| 40° C. | −0.05 | −0.04 | −0.03 | −0.02 | −0.03 | −0.02 | −0.04 | −0.04 | −0.08 | −0.15 | −0.12 |
| 60° C. | −0.25 | −0.08 | −0.07 | −0.07 | −0.08 | −0.14 | −0.18 | −0.24 | −0.46 | −0.50 | −0.87 |

As seen from the results of Table 3 and FIG. 1, firstly, it became obvious that the rate of change in HPLC purity can be held to 0.15% or less when the storage condition for $UP_4U$ crystals is one of the following conditions: (1) a storage temperature of 0° C. or more and less than 25° C.; (2) a storage temperature of 25° C. or more and less than 40° C. and a crystal pH of 4.5 to 8.0; and (3) a storage temperature of 40° C. or more and less than 60° C. and a crystal pH of 5.0 to 6.4.

Furthermore, it became obvious that the rate of change in HPLC purity can be held to 0.10% or less when the storage condition is one of the following conditions: (4) a storage temperature of 0° C. or more and less than 25° C.; (5) a storage temperature of 25° C. or more and less than 40° C. and a crystal pH of 4.5 to 7.4; and (6) a storage temperature of 40° C. or more and less than 60° C. and a crystal pH of 5.2 to 6.2.

Moreover, it became obvious that the rate of change in HPLC purity can be held to 0.05% or less when the storage condition is one of the following conditions: (7) a storage temperature of 0° C. or more and less than 25° C.; and (8) a storage temperature of 25° C. or more and less than 40° C. and a crystal pH of 4.6 to 6.6.

The invention claimed is:

1. A method for storing packed crystals of $P^1,P^4$-bis(5'-uridyl)tetraphosphate or a pharmaceutically acceptable salt thereof, wherein one of the following storage conditions (1) and (2): (1) a storage temperature of 0° C. or more and less than 40° C. and a crystal pH of 4.5 to 7.12; and (2) a storage temperature of 40° C. or more and less than 60° C. and a crystal pH of 5.2 to 6.2 is selected and the crystals of $P^1,P^4$-bis(5'-uridyl)tetraphosphate or the pharmaceutically acceptable salt thereof are stored under the selected condition so that a rate of decrease in HPLC purity of the crystals of $P^1,P^4$-bis(5'-uridyl)tetraphosphate or the pharmaceutically acceptable salt thereof at four weeks of storage is held to 0.1% or less.

2. A method for storing packed crystals of $P^1,P^4$-bis(5'-uridyl)tetraphosphate or a pharmaceutically acceptable salt thereof, wherein one of the following storage conditions (3) and (4): a storage temperature of 0° C. or more and less than 25° C. and a crystal pH of 4.5 to 7.12; and (4) a storage temperature of 25° C. or more and less than 40° C. and a crystal pH of 4.6 to 6.6 is selected and the crystals of $P^1,P^4$-bis(5'-uridyl)tetraphosphate or the pharmaceutically acceptable salt thereof are stored under the selected condition so that a rate of decrease in HPLC purity of the crystals of $P^1,P^4$-bis(5'-uridyl)tetraphosphate or the pharmaceutically acceptable salt thereof at four weeks of storage is held to 0.05% or less.

* * * * *

UNITED STATES PATENT AND TRADEMARK OFFICE
CERTIFICATE OF CORRECTION

PATENT NO. : 10,493,091 B2
APPLICATION NO. : 15/738108
DATED : December 3, 2019
INVENTOR(S) : Yusuke Ohba, Kentaro Miyoshi and Fumitaka Kano Page 1 of 1

It is certified that error appears in the above-identified patent and that said Letters Patent is hereby corrected as shown below:

In the Claims

In Column 8, Line 24 should read:
and (4): (3) a storage temperature of 0° C. or more and less than Signed and Sealed this
Fifth Day of May, 2020

Andrei Iancu
*Director of the United States Patent and Trademark Office*